US009285343B2

(12) United States Patent
Wu et al.

(10) Patent No.: US 9,285,343 B2
(45) Date of Patent: Mar. 15, 2016

(54) MULTI-DIMENTIONAL ION MOBILITY SEPARATOR METHOD AND APPARATUS

(71) Applicants: Ching Wu, Boxborough, MA (US); Christopher Hilton, Reno, NV (US)

(72) Inventors: Ching Wu, Boxborough, MA (US); Christopher Hilton, Reno, NV (US)

(73) Assignee: Excellims Corporation, Acton, MA (US)

( * ) Notice: Subject to any disclaimer, the term of this patent is extended or adjusted under 35 U.S.C. 154(b) by 0 days.

(21) Appl. No.: 14/214,590

(22) Filed: Mar. 14, 2014

(65) Prior Publication Data

US 2014/0346339 A1 Nov. 27, 2014

Related U.S. Application Data

(63) Continuation-in-part of application No. 13/651,837, filed on Oct. 15, 2012.

(60) Provisional application No. 61/784,470, filed on Mar. 14, 2013.

(51) Int. Cl.
*H01J 49/40* (2006.01)
*G01N 27/62* (2006.01)
*C07B 63/00* (2006.01)

(52) U.S. Cl.
CPC .............. *G01N 27/624* (2013.01); *C07B 63/00* (2013.01)

(58) Field of Classification Search
USPC .......................... 250/281, 282, 283, 285, 288
See application file for complete search history.

(56) References Cited

U.S. PATENT DOCUMENTS

| 2007/0176092 | A1* | 8/2007 | Miller | H01J 49/004 250/288 |
| 2009/0140140 | A1* | 6/2009 | Raznikov | G01N 27/622 250/287 |
| 2010/0001182 | A1* | 1/2010 | Burchfield | G01N 27/624 250/283 |
| 2010/0252435 | A1* | 10/2010 | Weber | G01N 27/44795 204/459 |

* cited by examiner

*Primary Examiner* — Phillip A Johnston
*Assistant Examiner* — Hsien Tsai

(57) ABSTRACT

One aspect of the present invention is to extract multiple ionic species in a FAIMS into one or more IMS drift tubes simultaneously. By adjusting FAIMS operational parameters, ions in FAIMS are detected on IMS detectors through separation in FAIMS and/or separation and collection in the IMS. This method provides a continuous separation of specific ions from an ion swarm by employing a high-field differential mobility analyzer (FAIMS) with a plurality of orthogonal transitions paths spaced incrementally along the electrodes which allow additional separation by a conventional IMS drift tube. The components of the sample can be collected or detected.

10 Claims, 5 Drawing Sheets

A

B

C

US 9,285,343 B2

MULTI-DIMENTIONAL ION MOBILITY SEPARATOR METHOD AND APPARATUS

The present application claims the benefit of and priority to corresponding U.S. Provisional Patent Application No. 61/784,470, filed on Mar. 14, 2013 and continuation in part of U.S. patent application Ser. No. 13/651,837 filed on Oct. 15, 2012, respectively, the entire content of the applications are herein incorporated by reference.

BACKGROUND OF THE INVENTION

Many hyphenated analytical instruments have been used to increase sample separation by utilizing two methods. These hyphenated instruments are normally configured in a tandem arrangement, such as a tandem FAIMS-IMS, where the components of the samples are separated by varying the DC compensation voltage so that each component reaches the inlet hole of the IMS at different voltages. The FAIMS unit works as a scanable filter whereby only ions with specific mobility will pass through the inlet hole of the IMS. Although this tandem FAIMS-IMS increases the ability to separate the sample, the time of analysis is increased by needing to vary the DC compensation voltage in the FAIMS and the components of the sample that are filtered at a given time cannot be collected. In order to address this deficiency, the present invention utilizes multiple orthogonal IMS drift tubes to the FAIMS filter array such that components of the sample can enter different IMS drift tubes and be collected and/or detected while the DC compensation voltage is held constant.

SUMMARY OF THE INVENTION

One aspect of the present invention is to extract multiple ionic species in a FAIMS into one or more IMS drift tubes simultaneously. By adjusting FAIMS operational parameters, ions in FAIMS are detected on IMS detectors through separation in FAIMS and/or separation and collection in the IMS. This method provides a continuous separation of specific ions from an ion swarm by employing a high-field differential mobility analyzer (FAIMS) with a plurality of orthogonal transitions paths spaced incrementally along the electrodes which allow additional separation by a conventional IMS drift tube. The components of the sample can be collected or detected.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

DETAILED DESCRIPTION OF VARIOUS EMBODIMENTS

Figure 1:
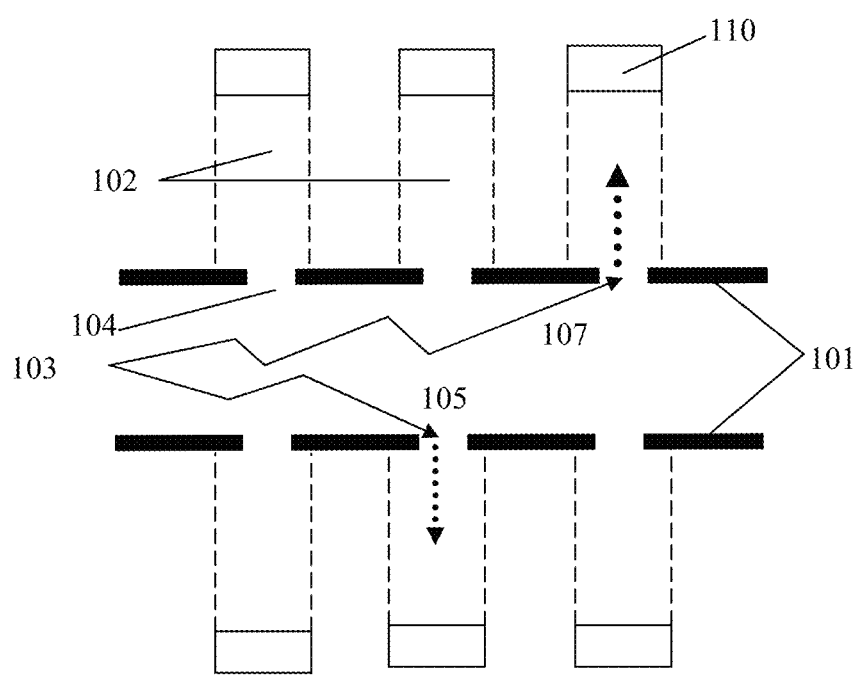
FIG. 1 shows two component mixtures of the sample being separated in the FAIMS into different orthogonal outlets.

A time of flight ion mobility spectrometer (IMS) and their derived forms refers to, in its broadest sense, any ion mobility based separation device that characterize ions based on their time of flight over a defined distance. A field asymmetric ion mobility spectrometer (FAIMS), a differential mobility spectrometer (DMS), and their derived forms separate ions based on their ion mobility characteristics under high values of normalized electric field. In general, in order for FAIMS to operate strong electric fields are required (10,000 volts/cm). A periodic electric waveform is applied to conductive surfaces about 2 mm apart and the wave form is asymmetric. FAIMS has been used as an ion separation technology, ion focusing device, and a atmospheric ion trap. In FAIMS the ions are separated according to their properties while drifting between two metal plates in very high electric fields. The application of high voltage in an appropriate waveform to the plates will create a condition where some types of ions drift and hit the metal plates while other types of ions remain between the plates. The ions that remain between the plates are balanced so that they reach a detector at the end or are sent into another device. Therefore the FAIMS unit works as a scanable filter whereby only ions with specific mobility will pass or be detected.

The systems and methods of the present inventions may make use of "drift tubes" as well as the FAIMS or DMS device. The term "drift tube" is used herein in accordance with the accepted meaning of that term in the field of ion mobility spectrometry. A drift tube is a structure containing a neutral gas through which ions are moved under the influence of an electrical field. It is to be understood that a "drift tube" does not need to be in the form of a tube or cylinder. As understood in the art, a "drift tube" is not limited to the circular or elliptical cross-sections found in a cylinder, but can have any cross-sectional shape including, but not limited to, square, rectangular, circular, elliptical, semi-circular, triangular, etc.

Neutral gas is often referred to as a carrier gas, drift gas, buffer gas, etc. and these terms are considered interchangeable herein. The gas is at a pressure such that the mean free path of the ion, or ions, of interest is less than the dimensions of the drift tube. That is the gas pressure is chosen for viscous flow. Under conditions of viscous flow of a gas in a channel, conditions are such that the mean free path is very small compared with the transverse dimensions of the channel. At these pressures the flow characteristics are determined mainly by collisions between the gas molecules, i.e. the viscosity of the gas. The flow may be laminar or turbulent. It is preferred that the pressure in the drift tube is high enough that ions will travel a negligible distance, relative to the longitudinal length of the drift tube, therefore a steady-state ion mobility is achieved.

The phrase "and/or," as used herein in the specification and in the claims, should be understood to mean "either or both" of the elements so conjoined, i.e., elements that are conjunctively present in some cases and disjunctively present in other cases.

One aspect of the present invention is to extract multiple ionic species in a FAIMS into one or more IMS drift regions for collection or detection. In particular, IMS drift regions are substantially orthogonal to the FAIMS filter array. The IMS drift regions could be used in either positive or negative operational modes. The locations where ions are ejected from the FAIMS represent their high E/N (field/number of molecules per volume) mobility property and the drift time in the IMS represents their low E/N mobility property. By adjusting FAIMS operational parameters, such as frequency, compensation voltage, etc., ions (either positive or negative) in the FAIMS are collected, detected, and or transferred to another instrument in an ion accumulator through separation in the FAIMS and IMS.

One embodiment of the present invention is a method for the continuous separation of specific ions from an ion swarm by employing a FAIMS with a plurality of orthogonal transitions paths spaced incrementally along the electrodes which allow additional separation by a conventional IMS drift tube. By adjusting FAIMS operational parameters, ions in FAIMS are detected on IMS detectors through separation in FAIMS and the IMS. When the ionized components are in the FAIMS spaced electrode array, the components of the sample can be distributed across the FAIMS spaced electrode array into the largest distribution by optimizing the DC compensation voltage such that each component can enter different orthogonal IMS drift regions. FIG. 1 shows a non-limiting example of the apparatus that has 4 sets of electrodes 101 in an array whereby the IMS drift regions 102 are substantially orthogonal to the gap 104 between these electrodes 101 in the FAIMS. The ionized sample 103 is separated in the FAIMS into different sample component mixtures. The sample can be ionized by a number of ionization sources such as electrospray, corona discharge, UV, atmospheric pressure photoionization (APPI), Ni63 or others. In addition, the sample can be also be added to the apparatus without an ionization source if the sample is already in an ion state. In this non-limiting case, there are two component mixtures that are separated from the sample in the FAIMS. The first component mixture 105 of the sample enters one IMS drift region, while the second component mixture 107 of the sample enters another IMS drift region. Each of these component mixtures of the sample can be further separated in the IMS drift region. The separated components of the component mixture in the IMS can be collected, detected, and or transferred to another instrument in the ion accumulator 110. When collecting, the ion accumulator can collect in a static or dynamic mode. If the FAIMS separation is good enough to separate individual components of the sample into a individual IMS drift regions, then further separation in the this IMS drift region would not be needed.

Figure 2A:
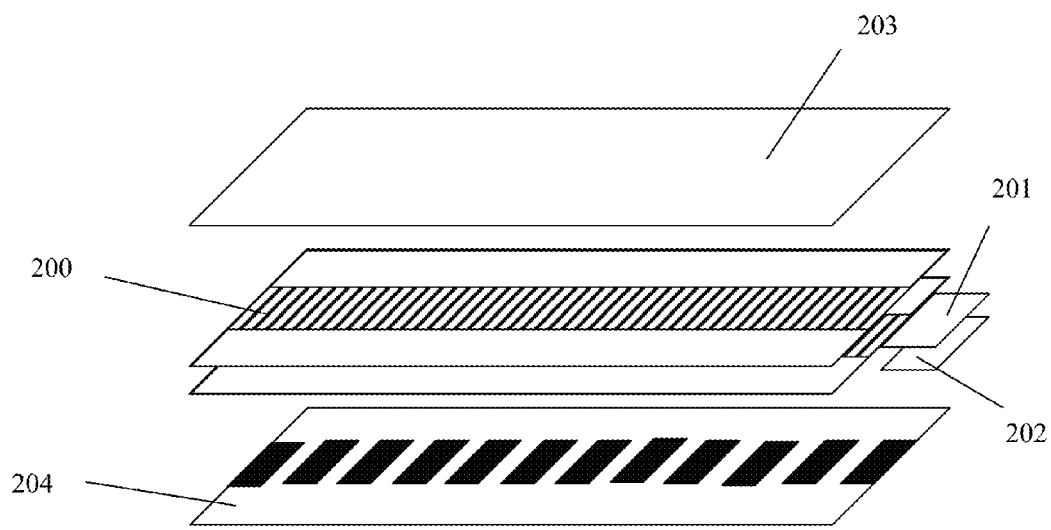
FIG. 2A-B shows the ionized sample can be pre-selected into an analytical gap between electrodes with conditions favorable for separation of positive or negative ions.
Figure 2B:
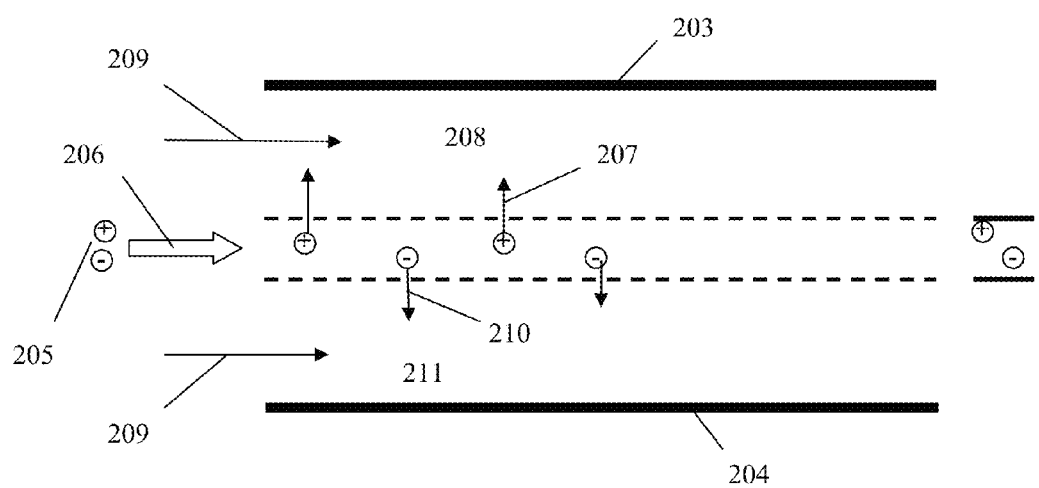

Another embodiment of the present invention is to have the IMS drift regions on either side of the FAIMS spaced electrode array in either positive or negative mode to accept ions. Therefore all ionic species (or more than one) can be simultaneously separated. A non-limiting example is shown in FIGS. 2A-B. FIG. 2A shows some of the components of the apparatus: two grids 200 of incrementally spaced electrodes, with a positive FAIMS detector 201 and a negative FAIMS detector 202, and a positive IMS detector plate 203 and a negative IMS detector plate 204. FIG. 2B shows the movement of the ions through the apparatus. The sample 205 is carried by a high gas flow 206 into the FAIMS and positive ions are ejected 207 into the positive IMS region 208 where there is a cross drift gas flow 209 for the IMS. The positive ions are further separated in the IMS if necessary and are detected on the positive detector plate 203. The negative ions are ejected 210 into the negative IMS region 211 where there is a cross drift gas flow 209 for the IMS. The negative ions are further separated in the IMS if necessary and are detected on the negative detector plate 204. In addition, ions can be detected on the positive FAIMS detector 201 or the negative FAIMS detector 202.

Figure 3:
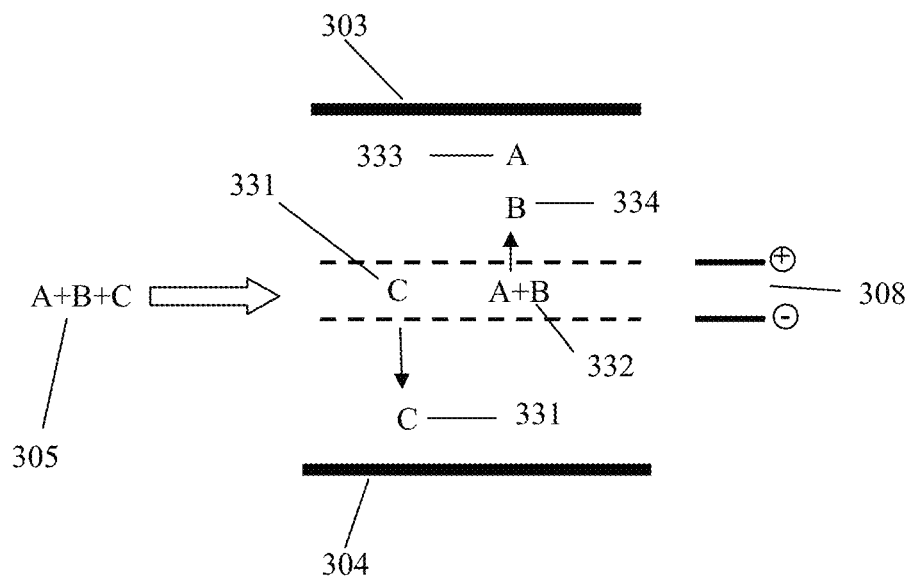
FIG. 3 shows an example of the FAIMS separation and IMS separation of three components A, B, and C of a sample.
Figure 3:
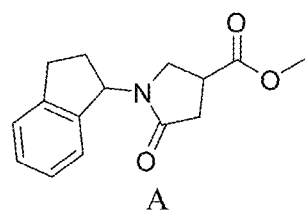
Figure 3:
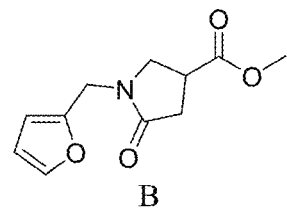
Figure 3:
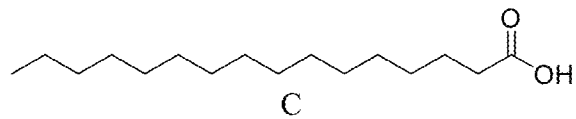

A specific example is shown in FIG. 3 where the components of a sample A, B, and C are partially separated in the FAIMS high field portion and then are further separated in the low field IMS in order to achieve complete separation of the components of the sample. The sample 305 (A+B+C) are added to the apparatus as ions or are ionized using various ionization sources such as electrospray, corona discharge, UV, atmospheric pressure photoionization (APPI), Ni63 or others. The components of the sample 305 have different functional groups which dictate which individual component will be a positive ion or a negative ion. Components A and B are both positive ions and component C is a negative ion due to the acid group functionality. The DC compensation voltage is set so that the components of the sample 305 are distributed across the FAIMS spaced electrode array moving towards the positive FAIMS detector the negative FAIMS detector 308. Components A+B 332 are not separated from each other using only the FAIMS high field separation, although component C 331 is separated from components A+B 332. Therefore only partial separation of the sample 305 is achieved using only the FAIMS high field separation. Component C 331 and components A+B 332 enter a different orthogonal IMS drift region which corresponds to the components charge state (positive or negative). Component C 331 travels through the orthogonal IMS drift region and is detected on the negative IMS detector plate 304. Components A+B 332 travels through another orthogonal IMS drift region under a low field. Components A+B 332 are separated into individual species, component A 333 and component B 334 by utilizing the low field separation of the IMS and are detected on the positive IMS detector plate 303. The components can be collected as well as detected using an ion accumulator in place of the detector plates 303 and 304. This example shows that the simultaneous separation using FAIMS and IMS in a substantially orthogonal configuration provides an apparatus and method for separating components of a sample using both high and low field IMS.

Figure 4:
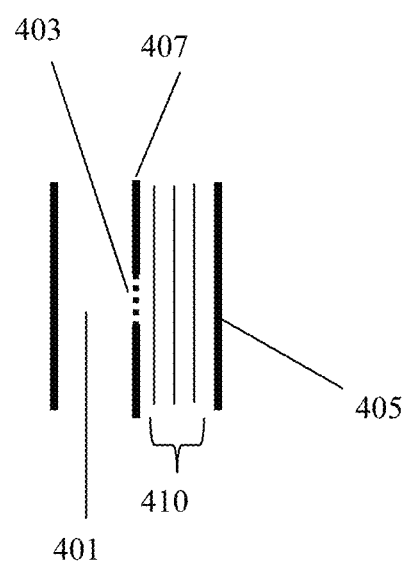
FIG. 4 shows a three electrode plate IMS.

Another aspect of the present invention is to use a high voltage on a limited number of electrodes in a IMS so that the length of the drift tube (drift region) can be reduced providing equal separation characteristics as the currently used 10 to 30 cm length. The drift tube length can be 5-15 times shorter that what is currently used. One embodiment of the invention uses only 3 electrode plates in the design. FIG. 4 shows a non-limiting drawing of the apparatus. The apparatus can be used alone as a single IMS or together with a FAIMS. The sample is introduced in the ionization region 401 before the gate 403. The sample is then ionized and travels to the detector electrode 405 from the gate electrode 407 by the applied voltage on these two electrodes. The sample component ions are separated while traveling across the field lines 410 to the detector electrode 405.

Figure 5A:
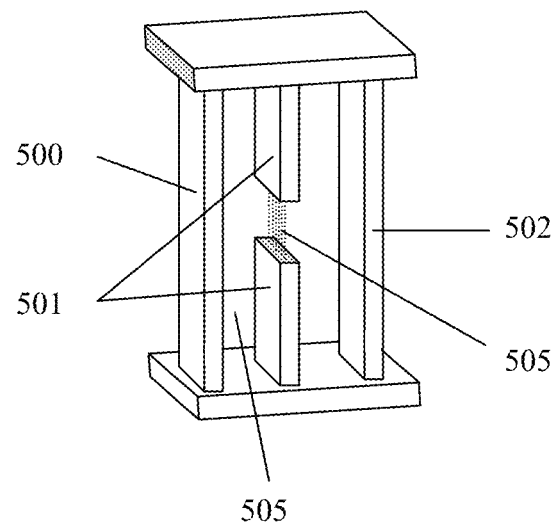
FIG. 5A-B shows two views of the 3 plate IMS; 5A shows a side view and 5B shows a front view linked together by the walls to form a honeycomb like structure.
Figure 5B:
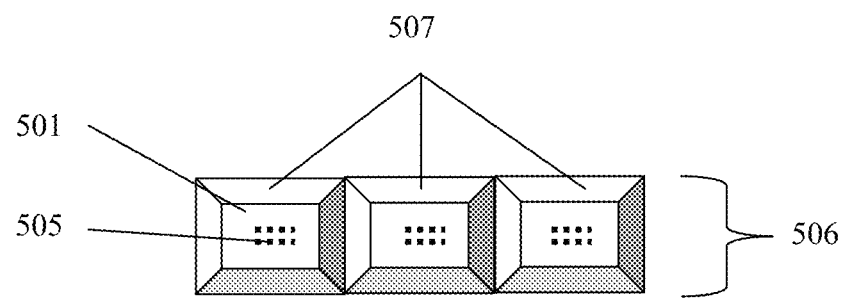

The apparatus can be fabricated in a number of ways. For example, 3 or more plates can be sandwiched together to form the enclosure as shown in FIG. 5A. FIG. 5A shows a side view of the apparatus with 3 isolated plates 500, 501, and 502 without the side walls of the apparatus. The ionization region 505 is located between plates 500 and 501. Plate 501 has is the electrode that consists of the gate 505. Plate 502 is the detector electrode. The apparatus can be linked together by the walls to form a honeycomb like structure shown in FIG. 5B. FIG. 5B shows a front view of the apparatus showing plate 501 with the gate 505 where plates 500 and 502 are not shown. The side walls 506 are linked together to form a six individual drift regions 507. The detector plate can be in individual sections for each drift region or used as a single detector plate to detect the ions for all of the drift regions.

What is claimed is:
1. An apparatus for the separation of components in a sample comprising:

(a) a differential ion mobility spectrometer with a plurality of outlets substantially orthogonal to a first sample flow path, wherein the outlets are located before the end of the separation section of the differential ion mobility spectrometer;
(b) a plurality of time of flight ion mobility spectrometers simultaneously receiving ions leaving from the outlets; and
(c) a plurality of ion accumulators in fluid communication with the time of flight ion mobility spectrometer and positioned to receive ions leaving the time of flight ion mobility spectrometer.

2. The apparatus of claim 1, wherein the differential ion mobility spectrometer has a DC compensation voltage that is held constant.

3. The apparatus of claim 2, wherein the DC compensation voltage is set at a level whereby the components are in a spatial distribution.

4. The apparatus of claim 1, wherein the differential ion mobility spectrometer has a plurality of electrodes in an array.

5. The apparatus of claim 4, wherein the plurality of time of flight ion mobility spectrometers are spaced incrementally along the electrode array.

6. The apparatus of claim 5, wherein the plurality of time of flight ion mobility spectrometers are substantially orthogonal to the first sample flow path.

7. The apparatus of claim 1, wherein the differential ion mobility spectrometer separates the sample with a high E/N mobility property.

8. The apparatus of claim 1, wherein the time of flight ion mobility spectrometer separates the sample with a low E/N mobility property.

9. A method for the separation of components in a sample comprising:
(a) separating at least one component in a differential ion mobility spectrometer using a high field with a plurality of outlets substantially orthogonal to a first sample flow path, wherein the outlets are located before the end of the separation section of the differential ion mobility spectrometer;
(b) simultaneously receiving ions leaving the outlets with a plurality of time of flight ion mobility spectrometers;
(c) separating at least one component in a time of flight ion mobility spectrometer using a low field; and
(d) receiving ions leaving the time of flight ion mobility spectrometer with a plurality of ion accumulators in fluid communication with the time of flight ion mobility spectrometer.

10. The method of claim 9, further comprises scanning and then setting the DC compensation voltage at a level where the components of the sample are separated in the largest spatial distribution in the high field.

* * * * *